(12) United States Patent
Hickle

(10) Patent No.: US 7,367,339 B2
(45) Date of Patent: May 6, 2008

(54) NEURAL NETWORKS IN SEDATION AND ANALGESIA SYSTEMS

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 741 days.

(21) Appl. No.: 10/677,484

(22) Filed: Oct. 3, 2003

(65) Prior Publication Data

US 2004/0129271 A1 Jul. 8, 2004

Related U.S. Application Data

(60) Provisional application No. 60/415,525, filed on Oct. 3, 2002.

(51) Int. Cl.
*A61M 11/00* (2006.01)
(52) U.S. Cl. .............. 128/204.23; 128/204.18; 128/204.22; 604/66
(58) Field of Classification Search ........... 128/203.12, 128/204.18, 204.22, 204.23, 924, 925, DIG. 12, 128/DIG. 13; 600/300, 534, 535, 544; 604/64, 604/65, 66; 706/15, 16, 22, 25
See application file for complete search history.

(56) References Cited

U.S. PATENT DOCUMENTS

| | | | |
|---|---|---|---|
| 4,570,640 A | 2/1986 | Barsa | |
| 5,251,626 A * | 10/1993 | Nickolls et al. | 607/14 |
| 5,309,921 A | 5/1994 | Kisner et al. | |
| 5,339,818 A | 8/1994 | Baker et al. | 128/677 |
| 5,352,195 A * | 10/1994 | McEwen | 604/66 |
| 5,953,713 A | 9/1999 | Behbehani et al. | |
| 6,190,328 B1 | 2/2001 | Ruton et al. | |
| 6,317,627 B1 | 11/2001 | Ennen et al. | |
| 6,431,171 B1 * | 8/2002 | Burton | 128/204.18 |
| 6,594,524 B2 * | 7/2003 | Esteller et al. | 607/45 |
| 6,658,396 B1 * | 12/2003 | Tang et al. | 706/17 |
| 6,678,669 B2 * | 1/2004 | Lapointe et al. | 706/15 |

OTHER PUBLICATIONS

International Search Report dated Sep. 2, 2004 for International Application No. PCT/US03/31909.

* cited by examiner

*Primary Examiner*—Steven O. Douglas
(74) *Attorney, Agent, or Firm*—Hogan & Hartson LLP

(57) ABSTRACT

The present invention comprises systems and methods for handling large amounts of data prone to ambiguity and artifact in real-time in order to ensure patient safety while performing a procedure involving a sedation and analgesia system. The invention utilizes neural networks to weight data which may be more accurate or more indicative of true patient condition such that the patient condition reported to the controller and the user of a sedation and analgesia system will have increased accuracy and the incidence of false positive alarms will be reduced.

12 Claims, 3 Drawing Sheets

NEURAL NETWORKS IN SEDATION AND ANALGESIA SYSTEMS

CROSS REFERENCE TO RELATED APPLICATIONS

This application claims priority under 35 U.S.C. §119(e) to U.S. Provisional Patent Application No. 60/415,525, "Neural Networks in Sedation and Analgesia Systems," filed Oct. 3, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to neural networks and, more particularly, to neural networks incorporated into sedation and analgesia systems.

2. Description of the Related Art

A sedation and analgesia system has been developed to provide patients undergoing painful, uncomfortable or otherwise frightening (anxiety inspiring) medical or surgical procedures with a means for receiving sedative, analgesic, and/or amnestic drugs safely in a way that reduces the risk of overmedication with or without the presence of a licensed anesthesia provider. Due to significant advances in technology, the sedation and analgesia system may be safer for use in hospital and ambulatory environments and may be operated by individuals other than trained anesthesiologists such as, for example, C.R.N.A.s, trained physicians, or other trained operators. The sedation and analgesia system has gone far to meet the needs of practitioners who are unable to schedule anesthesia providers for every procedure where safe and effective sedation and analgesia could substantially mitigate the effects of fear and pain. The advent of a sedation and analgesia system devoted to these purposes provides these individuals with a drug delivery system integrated into a patient monitoring system that decreases the cognitive and manual workload required with the operation of anesthesia machines, yet keeps the clinician in the loop of patient management. The clinician maintains ultimate decision making responsibility following a "clinician knows best" philosophy. This advanced technology allows for the sedation and analgesia system to be operated at drug level effects less than general anesthesia without an anesthesia provider, providing the patient with a cost-effective and readily available means of sedation, amnesia, and/or analgesia.

An example of a sedation and analgesia system is described in U.S. patent application Ser. No. 09/324,759, filed Jun. 3, 1999 and incorporated herein by reference in its entirety. This sedation and analgesia system electronically integrates, for example, the delivery of one or more sedative, analgesic, and/or amnestic drugs, the delivery of positive airway pressure, decreases or increases in drug delivery, the delivery of oxygen, changes in drugs to, for example, an opioid antagonist, requests for additional information from patient monitors, and the triggering of alarms, with the electronic monitoring of one or more patient physiological conditions. In one form, the system of the '759 application uses one or more sets of stored data-defining parameters reflecting patient and system states, the parameters being accessed through software to conservatively manage and correlate drug delivery to safe, cost effective, optimized values related to the conscious patient's vital signs and other physiological conditions.

As the computational and decision making capabilities of such integrated monitoring and drug delivery systems are escalated, accurate data analysis plays an increasingly crucial role in ensuring patient safety. Often, such systems are programmed to monitor increasingly complex data that may be prone to ambiguity or artifact with traditional Von Neumann machines. In response to this, software development has largely been slowed in areas such as waveform monitoring where extensive time and money is spent on developing sophisticated algorithms that may still not operate satisfactorily.

A further problem with conventional approaches to handling complex data is that they are frequently computationally expensive which either necessitates enormous computing power, or simply precludes their use in systems which must perform in real-time. For example, in the analysis of physiological waveforms, real time performance is often essential to achieve results fast enough to take corrective responses to abnormalities in a patient's physiological condition.

Neural network architectures, which are loosely based on knowledge of the neuroanatomy of the brain, have been shown to perform well at tasks such as the classification of waveforms having subtle differences-tasks which heretofore have been limited to performance by humans. In addition to their robust ability to recognize characteristic waveforms which vary widely from predicted shapes, neural networks may offer solutions to other aspects of data analysis in sedation and analgesia systems. Neural networks need not require explicit algorithms to analyze the large and potentially spurious and ambiguous data created by comprehensive patient monitoring. Instead, these systems, trained with exemplars, converge to an acceptable solution. In addition, once trained, a neural network can generally perform a recognition task rapidly due to its inherent parallelism.

SUMMARY OF THE INVENTION

The present invention comprises systems and methods for handling large amounts of data prone to ambiguity and artifact in real-time in order to ensure patient safety while performing a procedure involving a sedation and analgesia system. The invention utilizes neural networks to weight data which may be more accurate or more indicative of true patient condition such that the patient condition reported to the controller and the user of a sedation and analgesia system will have increased accuracy and the incidence of false positive alarms will be reduced. Such systems may be trained by using data recorded from prior medical procedures until the systems can accurately detect and distinguish between normal and adverse patient conditions.

DETAILED DESCRIPTION OF THE INVENTION

Figure 1:
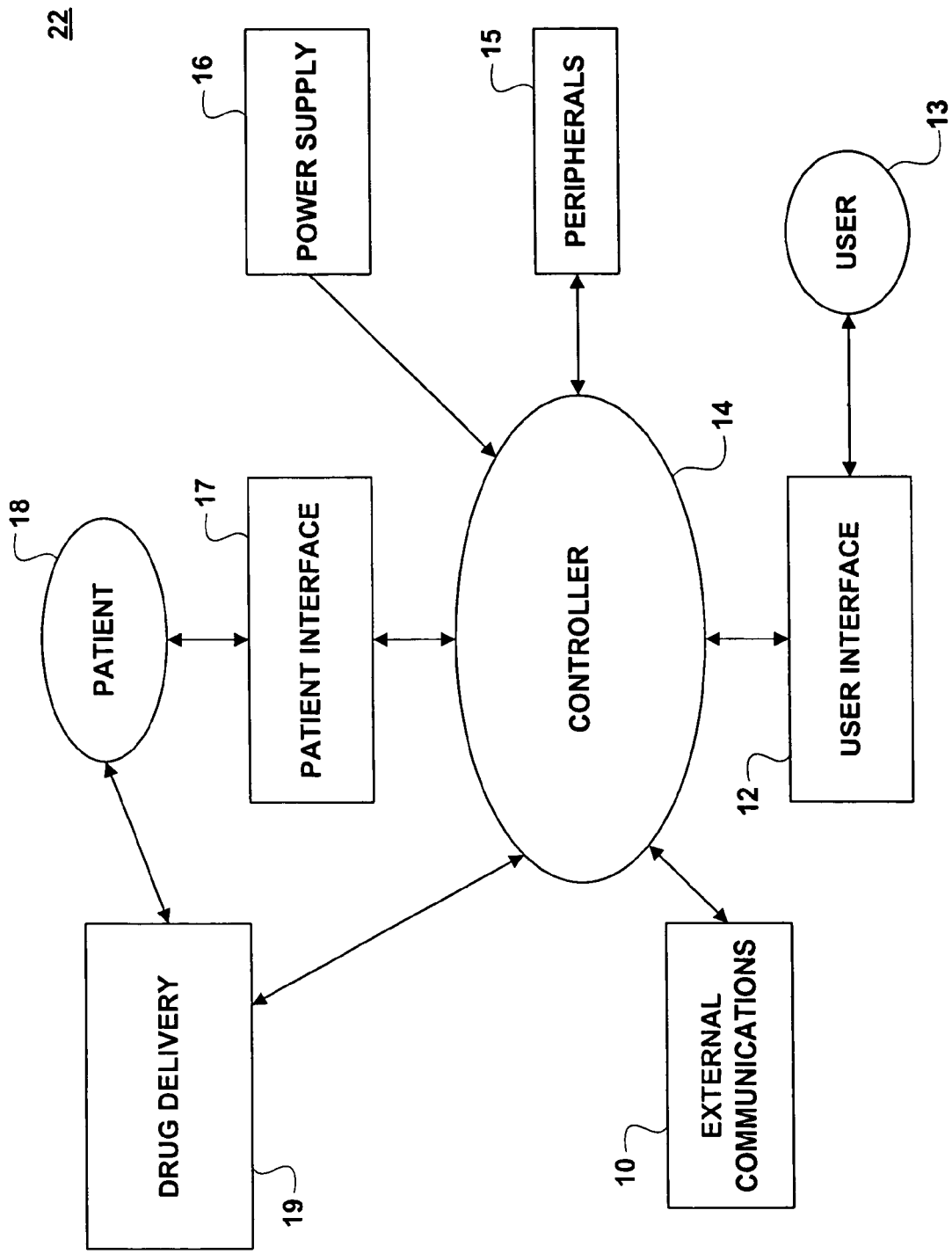
FIG. 1 illustrates a block diagram depicting one embodiment of a sedation and analgesia system in accordance with the present invention.

FIG. 1 illustrates a block diagram depicting one embodiment of a sedation and analgesia system 22 in accordance with the present invention having user interface 12, software controlled controller 14, peripherals 15, power supply 16, external communications 10, pressure delivery 11, patient interface 17, and drug delivery 19, where sedation and analgesia system 22 is operated by user 13 in order to provide sedation and/or analgesia to patient 18. An example of sedation and analgesia system 22 is disclosed and enabled by U.S. patent application Ser. No. 09/324,759, filed Jun. 3, 1999 and incorporated herein by reference in its entirety. Embodiments of user interface 12 are disclosed and enabled by U.S. patent application Ser. No. 10/285,689, filed Nov. 1, 2002 and incorporated herein by reference in its entirety.

Patient interface 17 includes one or more patient health monitors such as vital sign monitors and consciousness monitors including but not limited to non-invasive blood pressure monitors, pulse oximeters, capnometers, ECGs, patient consciousness assessment systems, ventilatory flow monitors, ventilatory pressure monitors, impedance plethysmographs (IPGs), gas analyzers, ventilatory temperature monitors, ventilatory humidity monitors, and acoustical monitors. The patient monitors of patient interface 17 may be electronically coupled to controller 14 and, through (for example) A-D converters, provide signals representing the patient's actual physiological condition. Such signals may be integrated into a neural network as will be further discussed herein.

Figure 2:
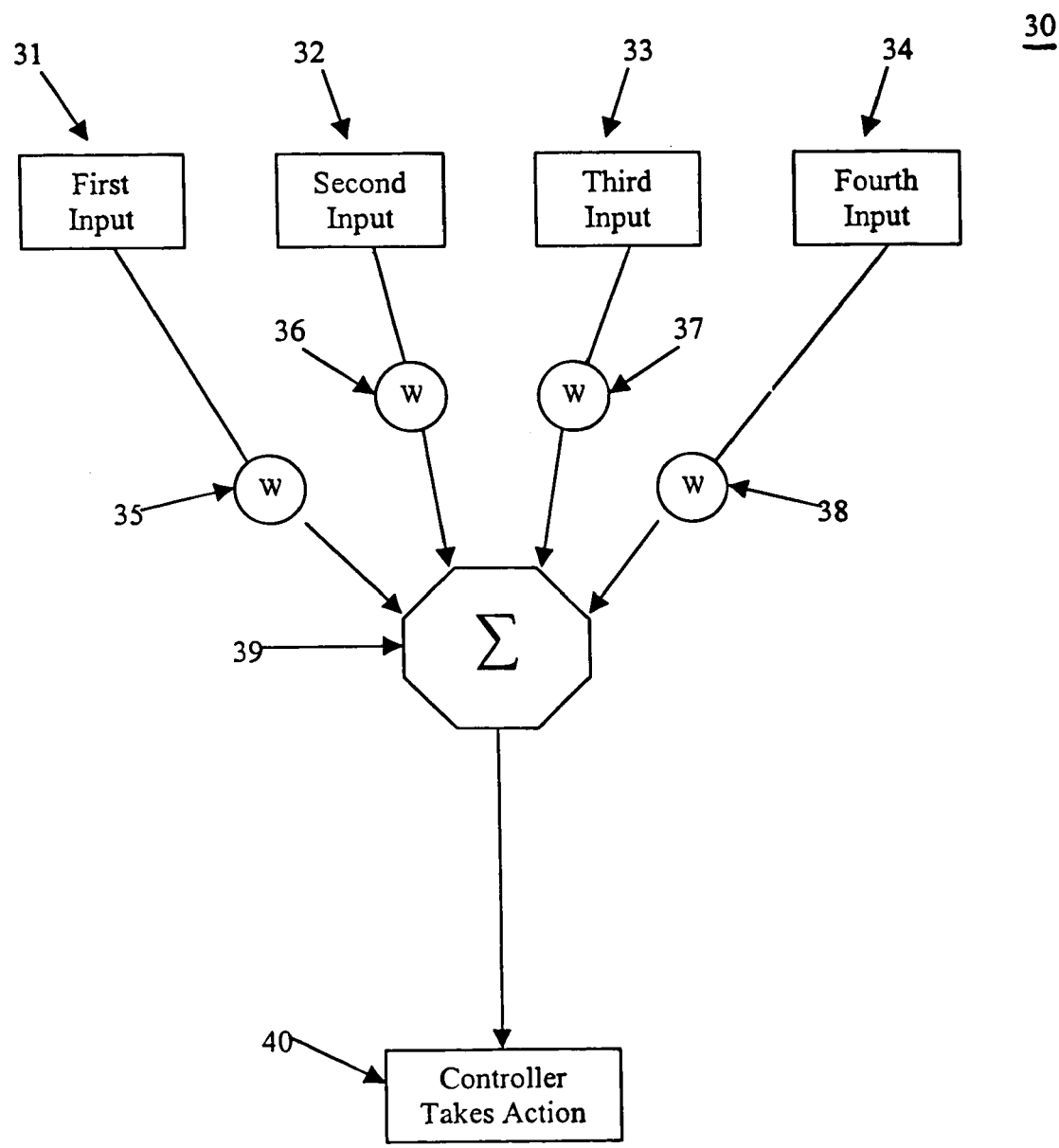
FIG. 2 illustrates one embodiment of a threshold logic unit in accordance with the present invention.

FIG. 2 illustrates one embodiment of a threshold logic unit (TLU) 30 in accordance with the present invention. In the illustrated example, input signals 31, 32, 33, and 34 are input into TLU 30. The effect input signals 31, 32, 33, and 34 have on controller action 40 may be determined by multiplying each input signal by a weight 35, 36, 37, and 38, respectively. The value of each input upon such multiplication indicates the strength of the synapse of input signals 31, 32, 33, and 34 within TLU 30. The input signals may, for example, take on the values of "1" or "0" only, where the signals are Boolean valued and may be used with digital logic circuitry and may be multiplied by any suitable weight corresponding to the significance of the signal. The number of input signals and corresponding weights may be expanded or contracted in accordance with the present invention to meet the demands placed on sedation and analgesia system 22.

For example, first input 31 may be from a sensor monitoring nasal airway pressure, second input 32 may be from a sensor monitoring oral airway pressure, third input 33 may be from a sensor monitoring nasal capnometry, and fourth input 34 may be from a sensor monitoring oral capnometry. TLU 30 may be employed to determine whether the patient is experiencing sufficient respiration. Weights 35, 36, 37, and 38 may be trained to be set at a value representative of the significance of each signal resulting from the corresponding input. For example, inputs 31, 32, 33, and 34 maybe binary signals, where a "1" is sent if a respiratory problem is detected by each of the sensors and a "0" is sent if the sensor determines everything to be satisfactory. Greater weights may then be given to those sensors more likely to accurately detect an adverse patient condition. Once such weights have been established, the values of the inputs 31, 32, 33, and 34, multiplied by the weights 35, 36, 37, and 38, respectively, may be summed by sigma 39. Sigma 39, based on the weighted input signals may then, for example, ascertain whether the sum is above an established threshold number (e.g., 1), indicative of an adverse respiratory condition. Action 40 of TLU 30 comprises taking action based on the sum calculated at sigma 39. If the calculation is above the threshold, TLU 30 may initiate steps to alleviate the respiratory condition. Examples of such steps initiated by TLU 30 include decreasing drug levels, increasing oxygen delivery, delivering a pharmacological antagonist, alarming clinicians, requesting additional patient information from patient monitors, testing patient responsiveness, delivering positive airway pressure, and/or any other suitable action. If the calculation of sigma 39 is less than the established threshold number, action 40 may maintain normal sedation and analgesia system functionality.

The present invention further comprises training TLU 30. This training, generally know in the art, comprises providing a series of inputs into TLU 30 indicative of various patient conditions, where the weights associated with TLU 30 are adjusted until the network accurately detects adverse patient conditions and retains normal functionality during non-critical situations. The present invention further comprises any suitable number of inputs from any suitable monitor or from any other suitable data source, where such inputs may transmit data in analog, digital, or any other suitable form.

Figure 3:
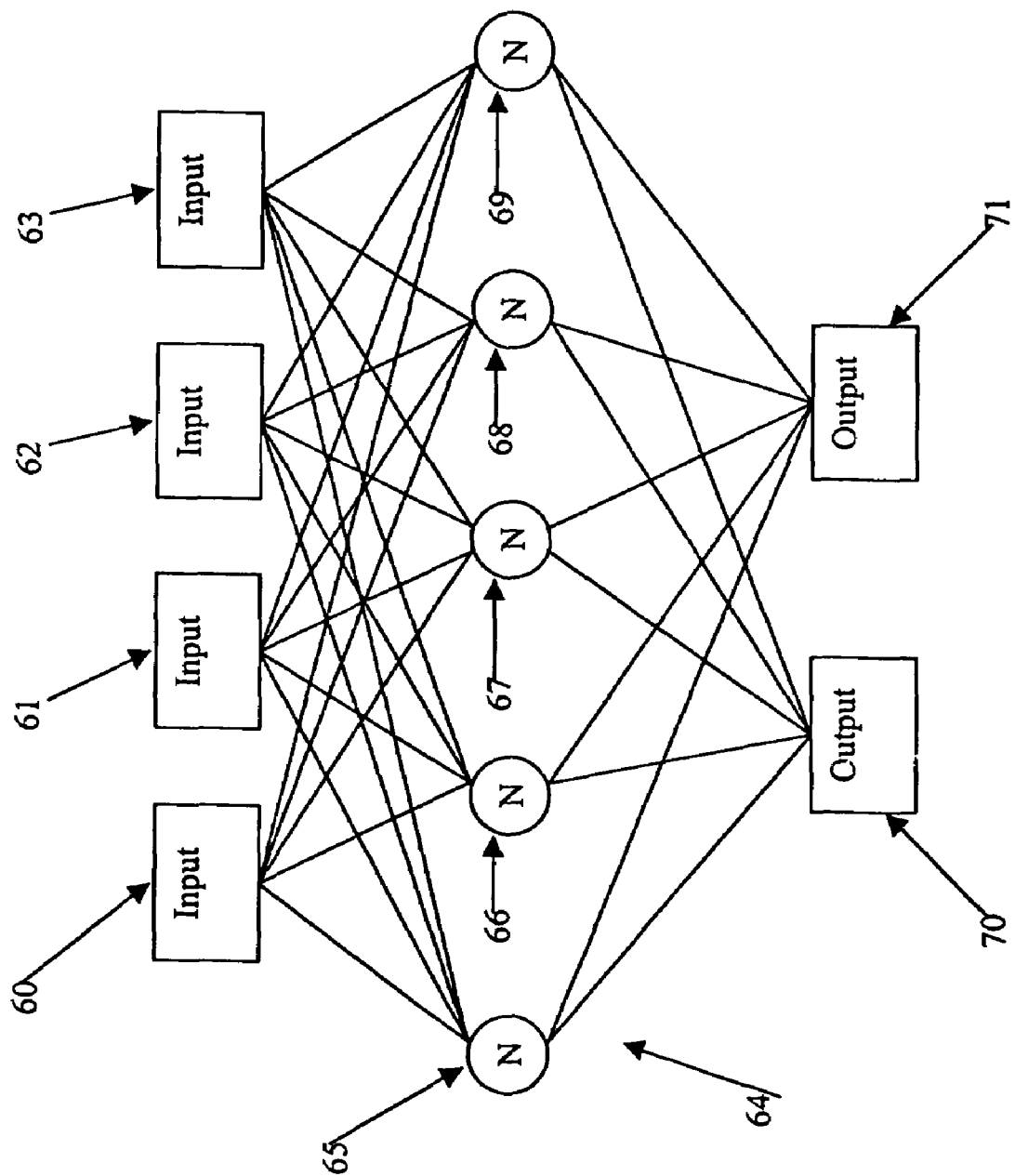
FIG. 3 illustrates one embodiment of a neural network in accordance with the present invention.

FIG. 3 illustrates one embodiment of a neural network 64 in accordance with the present invention. Neural network 64 comprises a set of inputs 60, 61, 62, and 63 that make up a first layer of nodes, a set of hidden nodes 65, 66, 67, 68, and 69, and a set of output nodes 70 and 71. Inputs 60, 61, 62 and 63 may be related to any suitable feature of patient monitoring. For example, in monitoring respiratory sufficiency, input 60 may be nasal ventilatory pressure, input 61 may be oral ventilatory pressure, input 62 may be nasal capnometry, and input 63 may be oral capnometry. Data from each input may then be passed to a hidden node 65, 66, 67, 68, and 69, where each signal may be weighted differently at each node in order to use the inherent parallelism of the neural network to accurately distinguish between normal and adverse patient conditions.

Data propagated to hidden nodes 65, 66, 67, 68 and 69 may be weighted by a numerical coefficient that indicates the significance of that characteristic. Neural network 64 then propagates such calculation to output nodes 70 and 71, and then provides a categorization of the data. The number of input nodes, hidden nodes, and output nodes may be expanded or contracted in accordance with the present invention to meet the demands placed on sedation and analgesia system 22. For example, neural network 64 may be used with multiple traits, multiple categorizations, multiple hidden layers, may receive inputs from other neural networks, and/or may use calculated data, such as the sum of squares of respiratory rate, as inputs. The present invention further comprises the training of neural network 64, where neural network 64 adjusts its numerical coefficients until it reduces its output error to an acceptable range (not shown on figure). Because of the parallel architecture, the system's performance is not dependent on perfect accuracy at any one input, hidden, or output node. It can tolerate a fault at an individual node, as in the presence of sparse, ambiguous, or spurious data, yet still correctly recognize a critical pattern.

Any suitable patient parameter or features of such patient parameters may be incorporated as inputs into neural network 64, such as, for example, data derived from sensor fusion, data derived from orthogonally redundant monitoring, data trends, heart rate, blood pressure, data from other neural networks, pulse oximetry, capnometry, acoustical monitoring, respiratory rate, and the sum of squares from various patient parameters over time. Sensor fusion is further described in commonly assigned and co-pending U.S.

application entitled "Systems and Methods for Providing Sensor Fusion," filed Oct. 3, 2003, which is herein incorporated by reference. Orthogonally redundant monitoring is further described in commonly assigned and co-pending U.S. application entitled "Methods and Systems for Providing Orthogonally Redundant Monitoring in a Sedation and Analgesia System," Filed Oct. 3, 2003, which is herein incorporated by reference.

Systems according to the present invention may be trained by using data recorded from medical procedures until sedation and analgesia system 22 accurately detects and distinguishes between normal and adverse patient conditions. Furthermore, the present invention comprises the incorporation of any suitable perception, back-propagated, or radial basis function network into sedation and analgesia system 22, where any suitable network that increases the accuracy of sedation and analgesia system 22 is in accordance with the present invention.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A sedation and analgesia system, comprising:
two or more patient health monitor devices adapted so as to be coupled to a patient and so as to each generate a separate input signal reflecting a parameter of a physiological condition of the patient;
a user interface;
a drug delivery controller for delivering a drug dosage rate of sedative to the patient during a procedure; and
an electronic controller interconnected with the patient health monitors, the user interface, and the drug delivery controller, wherein said electronic controller further comprises a threshold logic unit which receives said input signals, multiplies each of said input signals by a predetermined weight corresponding to each of said parameters to achieve a weighted input signal for each corresponding input signal, combines the weighted input signals, and compares the weighted input signals against a predetermined threshold value that correlates to safe and effective sedation during said procedure to determine an action of said electronic controller.

2. The sedation and analgesia system of claim 1, wherein said input signals are binary values.

3. The sedation and analgesia system of claim 1, wherein each of said predetermined weights is trained to be set at a value representative of the significance of each signal resulting from the corresponding input and wherein said training comprises providing a series of inputs into the threshold logic unit indicative of at least one patient condition and the predetermined weights are adjusted until the system accurately detects adverse patient conditions and retains normal functionality during non-critical situations.

4. The sedation and analgesia system of claim 1, wherein said action of said electronic controller comprises at least one of decreasing drug levels, increasing oxygen delivery, delivering a pharmacological antagonist, alarming clinicians, requesting additional patient information from patient monitors, testing patient responsiveness, and delivering positive airway pressure.

5. The sedation and analgesia system of claim 1, wherein said patient monitoring devices comprise at least two of a sensor monitoring nasal airway pressure, a sensor monitoring oral airway pressure, a sensor monitoring nasal capnometry, and a sensor monitoring oral capnometry.

6. A sedation and analgesia system, comprising:
two or more patient health monitor devices adapted so as to be coupled to a patient and so as to each generate a separate input signal reflecting a parameter of a physiological condition of the patient;
a user interface;
a drug delivery controller supplying one or more drugs to the patient; and an electronic controller interconnected with the patient health monitors, the user interface, and the drug delivery controller, said electronic controller receiving said input signals from the patient health monitors and comparing said input signals to parameters that indicate whether a given patient is experiencing or in danger of experiencing an undesirable patient condition while receiving said one or more drugs at said drug delivery rate, and said electronic controller thereby generating a signal reflecting the monitored physiological condition of the patient and indicating modifications of said drug delivery to avoid said undesirable patient condition during said medical procedure wherein said electronic controller further comprises a neural network to evaluate input signals to determine an action of said electronic controller, wherein said neural network comprises a set of inputs that make up a first layer of nodes, a set of hidden nodes, and a set of output nodes, wherein said inputs are related to any suitable feature of said patient health monitors.

7. The sedation and analgesia system of claim 6, wherein each said input signal is weighted differently at each node to use parallelism of the neural network to accurately distinguish between normal and adverse patient conditions.

8. The sedation and analgesia system of claim 7, wherein each input signal propagated to said hidden nodes is weighted by a numerical coefficient that indicates the significance of the respective parameter for said input signal.

9. The sedation and analgesia system of claim 8, wherein said neural network adjusts its numerical coefficients through multiple iterations until it reduces its output error to a predefined acceptable range.

10. The sedation and analgesia system of claim 6, wherein said inputs comprise at least one of data derived from sensor fusion, data derived from orthogonally redundant monitoring, data trends, heart rate, blood pressure, data from other neural networks, pulse oximetry, capnometry, acoustical monitoring, respiratory rate, and the sum of squares from patient parameters over time.

11. The sedation and analgesia system of claim 6, wherein said action of said electronic controller comprises at least one of decreasing drug levels, increasing oxygen delivery, delivering a pharmacological antagonist, alarming clinicians, requesting additional patient information from patient monitors, testing patient responsiveness, and delivering positive airway pressure.

12. The sedation and analgesia system of claim 6, further comprising the incorporation of at least one of a perception, back-propagated, and radial basis function network, wherein said at least one network increases the accuracy of sedation and analgesia system.

* * * * *